United States Patent
Pick et al.

(10) Patent No.: US 8,226,585 B2
(45) Date of Patent: Jul. 24, 2012

(54) BRACE HAVING INFLATABLE SUPPORT

(75) Inventors: Erez Pick, Roslyn Heights, NY (US); Fabian McCarthy, Jr., Basking Ridge, NJ (US); Michael Pinzur, Highland Park, IL (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 11/338,164

(22) Filed: Jan. 23, 2006

(65) Prior Publication Data
US 2006/0189907 A1    Aug. 24, 2006

Related U.S. Application Data

(60) Provisional application No. 60/646,416, filed on Jan. 21, 2005.

(51) Int. Cl.
*A61F 5/00* (2006.01)

(52) U.S. Cl. ............... 602/13; 602/23; 602/27; 128/882

(58) Field of Classification Search ............... 602/5–13, 602/20–21, 23, 27, 60–65; 128/847, 878–879; 2/16, 22, 59, 159–160, 162, 910–911, 917, 2/DIG. 3; 36/88, 89, 140
See application file for complete search history.

(56) References Cited

U.S. PATENT DOCUMENTS

| | | | |
|---|---|---|---|
| 3,083,708 A | | 4/1963 | Gottfried et al. |
| 3,164,152 A | * | 1/1965 | Nicoll ............................ 602/13 |
| 3,403,673 A | | 10/1968 | MacLeod et al. |
| 3,824,992 A | | 7/1974 | Nicholson et al. |
| 3,888,242 A | | 6/1975 | Harris et al. |
| 3,955,565 A | * | 5/1976 | Johnson, Jr. .................... 602/12 |
| 4,280,489 A | * | 7/1981 | Johnson, Jr. .................... 602/27 |
| 4,722,332 A | * | 2/1988 | Saggers ........................... 602/62 |
| 4,805,601 A | * | 2/1989 | Eischen, Sr. .................. 601/151 |
| 4,817,590 A | * | 4/1989 | Stancik, Jr. ........................ 602/8 |
| 5,078,128 A | | 1/1992 | Grim et al. |
| 5,088,478 A | * | 2/1992 | Grim ............................... 602/27 |
| 5,094,252 A | | 3/1992 | Stumpf |
| 5,125,400 A | * | 6/1992 | Johnson, Jr. .................... 602/13 |
| 5,139,475 A | * | 8/1992 | Robicsek ......................... 602/13 |
| 5,218,954 A | * | 6/1993 | van Bemmelen ............. 601/151 |
| 5,288,286 A | * | 2/1994 | Davis ................................. 602/6 |
| RE34,661 E | * | 7/1994 | Grim ............................... 602/27 |
| 5,329,705 A | * | 7/1994 | Grim et al. ........................ 36/88 |
| 5,348,530 A | * | 9/1994 | Grim et al. ...................... 602/13 |
| 5,366,439 A | * | 11/1994 | Peters ............................. 602/27 |
| 5,389,065 A | * | 2/1995 | Johnson, Jr. .................... 602/27 |
| 5,400,529 A | | 3/1995 | Bell et al. |
| 5,425,701 A | * | 6/1995 | Oster et al. ..................... 602/23 |
| 5,435,009 A | * | 7/1995 | Schild et al. ....................... 2/22 |
| 5,464,385 A | * | 11/1995 | Grim ............................... 602/27 |

(Continued)

FOREIGN PATENT DOCUMENTS

EP    0770368 A    5/1997

(Continued)

*Primary Examiner* — Patricia Bianco
*Assistant Examiner* — Keri J Nelson
(74) *Attorney, Agent, or Firm* — Ropes & Gray LLP

(57) ABSTRACT

The systems and methods provide or use a brace for patient's limb that includes, among other things, a non-inflatable, rigid, lower housing for supporting the sole of a patient's foot, and an inflatable load-bearing upper housing that is affixed to the lower housing. The brace may be adjustable and configured to be fitted to patients having limbs of differing sizes, to allow the patient to obtain a more closely fitted brace.

29 Claims, 11 Drawing Sheets

U.S. PATENT DOCUMENTS

| | | | |
|---|---|---|---|
| 5,489,259 A | 2/1996 | Jacobs et al. | |
| 5,577,998 A * | 11/1996 | Johnson et al. | 602/5 |
| 5,711,760 A * | 1/1998 | Ibrahim et al. | 601/149 |
| 5,813,144 A | 9/1998 | Prengler | |
| 5,833,639 A * | 11/1998 | Nunes et al. | 602/23 |
| 5,868,690 A * | 2/1999 | Eischen, Sr. | 601/151 |
| 6,228,044 B1 * | 5/2001 | Jensen et al. | 602/27 |
| 6,511,449 B2 * | 1/2003 | Burns et al. | 602/13 |
| 6,554,785 B1 * | 4/2003 | Sroufe et al. | 602/23 |
| 6,589,194 B1 | 7/2003 | Calderon et al. | |
| 6,682,497 B2 * | 1/2004 | Jensen et al. | 602/27 |
| 6,875,190 B2 * | 4/2005 | Reinhardt | 602/27 |
| 6,945,944 B2 * | 9/2005 | Kuiper et al. | 602/13 |
| 2001/0020142 A1 * | 9/2001 | Bird | 602/13 |
| 2002/0095105 A1 * | 7/2002 | Jensen | 602/27 |
| 2003/0171703 A1 * | 9/2003 | Grim et al. | 601/152 |
| 2004/0111048 A1 * | 6/2004 | Jensen et al. | 602/13 |
| 2004/0236258 A1 * | 11/2004 | Burns et al. | 602/13 |
| 2005/0020952 A1 * | 1/2005 | Pick et al. | 602/27 |
| 2005/0085755 A1 * | 4/2005 | Rabe | 602/27 |
| 2006/0004310 A1 * | 1/2006 | Parizot | 602/5 |
| 2006/0173393 A1 * | 8/2006 | Sailhen | 602/23 |

FOREIGN PATENT DOCUMENTS

| | | |
|---|---|---|
| GB | 1171361 A | 11/1969 |
| WO | WO-2005/074834 A | 8/2005 |

* cited by examiner

BRACE HAVING INFLATABLE SUPPORT

REFERENCE TO RELATED APPLICATIONS

This application claims the benefit of U.S. Provisional Patent Application Ser. No. 60/646,416, filed on Jan. 21, 2005, the teachings of which are hereby incorporated by reference herein in their entirety.

BACKGROUND

The invention relates generally to orthopedic devices and more particularly to orthopedic devices for treating a fracture or other injury to the limb. Braces commonly used to treat limb injuries such as fractures are typically constructed of plaster, stiff plastic, or other hard material. Although generally effective and easy to use, such braces and casts are not of optimal utility. In one aspect, standard braces come in standard sizes that are not optimally adjustable, particularly around the calf and lower leg regions of the patient. Such limitation manifests itself most often in instances where the patient is obese or is otherwise experiencing edema or swelling in the lower limb. In such instances, the patient's lower leg is often enlarged, typically on a permanent or semi-permanent basis compared to its natural size. As a result, the patient may be required to use a brace that is one or more sizes too large for the foot in order to accommodate the extensive girth around the lower leg.

Moreover, standard braces are often constructed of heavy material such as plastic or plaster. Over time, the weight of such braces can bother a patient and cause the patient to stop wearing the brace as directed by their physician.

Accordingly, there is a need for braces that are as effective as conventional braces, including inflatable walking braces, but are easier to fit and more easily worn during the treatment period.

SUMMARY

The braces described herein include an inflatable, load-bearing structure that encompasses at least a region of the user's limb, and can compress against a limb for the purpose of securing the patient's limb and to off-load pressures that may lead to inflammation, ulcers, or other conditions. The outer structure includes one or more inflatable external cells that, upon inflation, render the structure load-bearing without the need to use a stiff casing or other rigid stiffening member. The brace may optionally also include an internal bladder system that is supported by the external inflatable structure. In certain embodiments, the internal and external bladder systems are inflatable, such as by action of a hand pump, compressor device, a breathing straw, or other suitable device. Upon inflation, the brace will provide support to the limb it is applied to.

The brace is light-weight, breathable and easy to apply, and is adjustable so as to fit comfortably around a patient's arm or leg and on the patient's foot or hand, even in instances where the patient's obesity renders the arm or leg excessively large in comparison with the patient's foot or hand, a condition that would preclude standard-sized braces from fitting properly.

In certain embodiments, the outer structure is a combination of inflatable cells and flexible materials that facilitate the appropriate fit, support and ventilation of the patient's limb. One or more of the internal bladders may pressurize independently from the load-bearing inflation structure, or a single inflation device may be used to inflate both the internal bladders and the inflatable load-bearing outer structure in concert.

The braces described herein may be applied to an ankle, a wrist, an elbow or any other joint or limb of a patient.

BRIEF DESCRIPTION OF THE FIGURES

The foregoing and other objects and advantages of the invention will be appreciated more fully from the following further description thereof, with reference to the accompanying drawings wherein.

DESCRIPTION OF CERTAIN ILLUSTRATIVE EMBODIMENTS

Figure 1A:
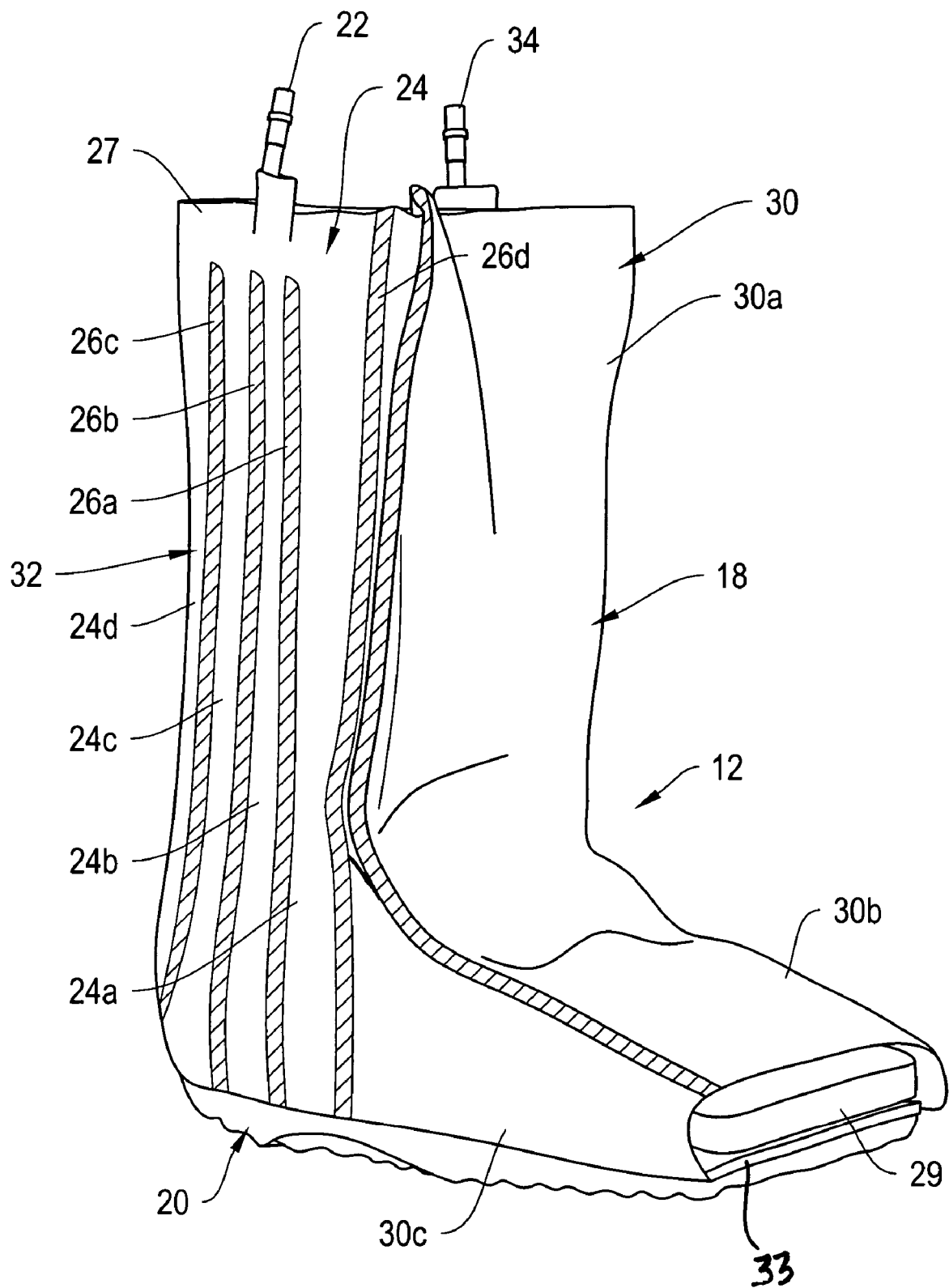
FIGS. 1A-1E depict right, front, top, side cross-sectional, and back views of a first embodiment of a lower-leg brace according to an illustrative embodiment of the invention.

To provide an overall understanding of the invention, certain illustrative embodiments will now be described. However, it will be understood by one of ordinary skill in the art that the systems and methods described herein can be adapted and modified for other suitable applications and that such other additions and modifications will not depart from the scope hereof.

More particularly, disclosed herein are soft, light-weight braces and methods for bracing an ankle, wrist or limb or joint and for manufacturing the braces described herein. The braces are adjustable and configured to be fitted to patients having limbs of differing sizes, particularly a patient whose arms or legs have excessive girth due to obesity, which impairs the patient from fitting into a brace that would otherwise appropriately fit the patient's hand or foot.

The braces include an inflatable load-bearing outer structure that can compress against a limb for the purpose of securing the limb to off-load pressures that may lead to inflammation, ulcers, or other conditions. The outer structure includes one or more inflatable external cells that, upon inflation, render the structure load-bearing to support the patient's injured limb without needing to use a stiff casing or other rigid stiffening member. The brace, may optionally also include an internal bladder system that is surrounded by and supported by the external inflatable structure.

FIGS. 1A-1E depict right, front, top, side cross-sectional, and back views of a first embodiment of an exemplary brace for a lower leg. In the depicted embodiment, the brace is an ankle boot 12 having an inflatable load-bearing upper housing 18 that is mechanically attached to a rocker sole bottom 20. The load-bearing structure 18 is adapted to inflate to provide a rigid structural support mechanism that is sized to fit the circumference of the patient's limb and that will support the patient's limb during treatment for fracture, edema and other injuries, and this without the need to use an outer casing or other metal or stiff plastic strengthening member. As shown, the load-bearing upper structure 18 includes a front panel 30 that extends from approximately the mid-region of the patient's shin down to the end of the patient's foot in approximately the region of the toes, and a rear panel 32 that extends from one side of the front panel 30 and around behind the patient's leg and is stitched or otherwise adjoined to the other side of the panel 30. The panels 30 and 32 are configured so that the upper structure 18 has a relatively large circumference, such that, when panels 30 and 32 are joined, the structure 18 can accommodate patient's limb, regardless of its girth. As explained below, after being applied to the limb, the panels 30 and 32 are inflated until they are sized to securely fit the circumference of the limb.

Figure 1B:
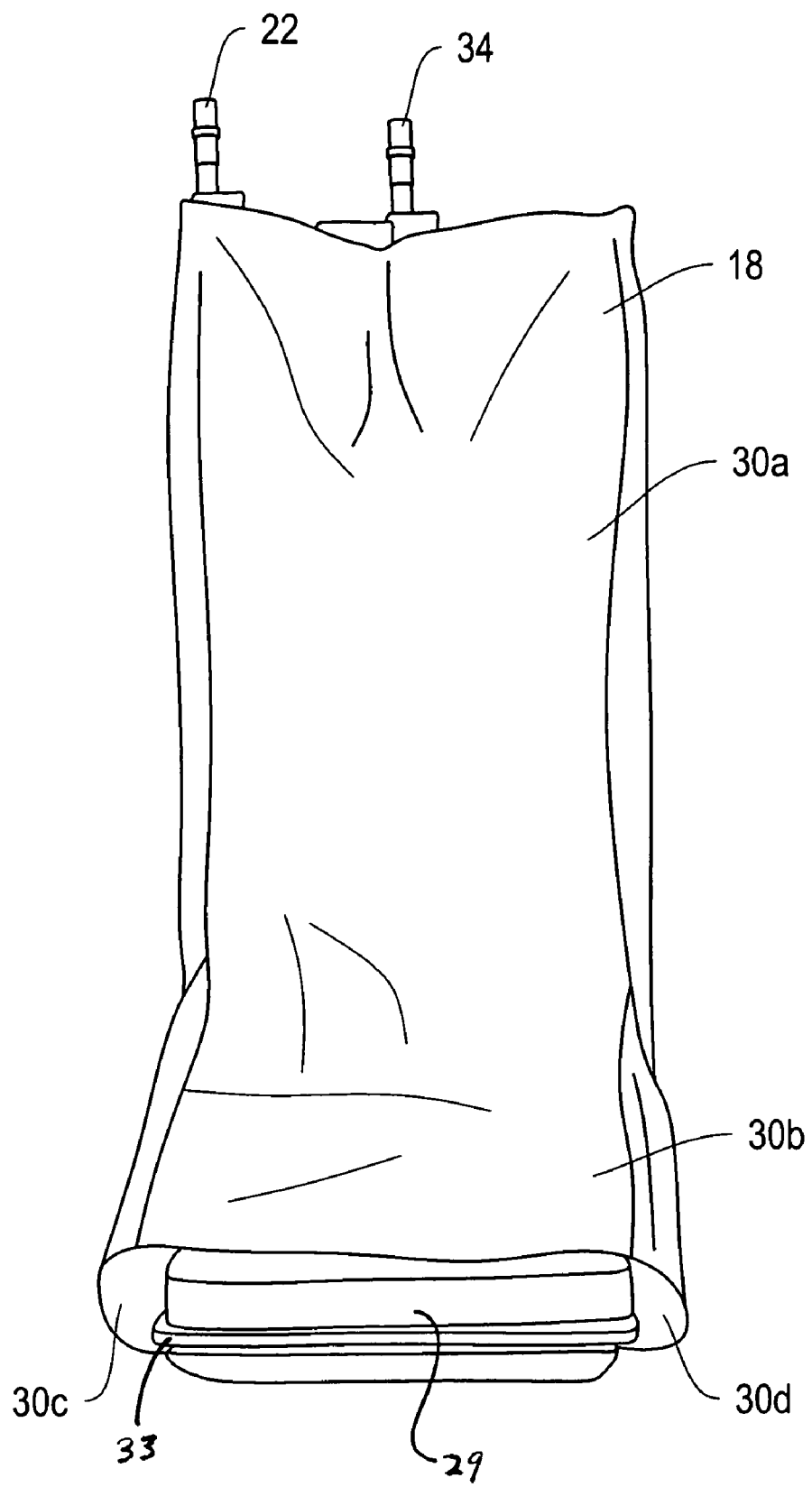

The front panel 30 of load-bearing structure 18 is an inflatable bladder region formed from a plurality of layers of urethane, nylon or other material that are stitched, bonded, or otherwise joined together to form inflatable regions 30a and 30b, and non-inflatable regions 30c and 30d. The inflatable regions 30a and 30b form a continuous bladder, with region 30a extending along the front side of the patient's leg and region 30b extending from approximately the top and upper sides of the patient's ankle and along the top of the patient's foot. Non-inflatable regions 30c and 30d extend along the respective sides of the patient's foot, as shown in FIG. 1B. In alternative embodiments, regions 30c and 30d are inflatable; they may also be continuous with region 30b. In the depicted embodiment, region 30c and/or 30d begin at a point that is distal to the user's ankle and extend toward the user's toes, such that the inflation regions 30a, 30b, and 32 envelop all of the user's ankle. In certain configurations, regions 30c and/or 30d begin at a point along the side or slightly proximal to the ankle and extend toward the user's toes, leaving the ankle substantially but not entirely enveloped by an inflation chamber. Such a configuration may be adapted, for example, where the patient desires to provide a brace that applies a reduced pressure to the sides of the foot to relieve blisters, ulcers, etc.

The rear panel 32 of load-bearing structure 18 includes right side 32a and left side 32b panels that are configured to releasably adjoin along a rear region 31 of the patient's leg by mechanical fastener 28. The panels 32a and 32b extend from the bottom sides of the patient's foot, above the heel and ankle, and up along the sides of the tibia into the region of the mid- or upper calf regions. The panels 32a and 32b are formed of a plurality of layers of urethane, nylon or other material that are stitched, bonded, or otherwise joined together to form an inflation bladder 24 having one or more fluid receiving regions. More particularly, the bladder region 24 includes a series of seams (e.g., seams 26a, 26b, 26c and 26d) that divide the rear panel 32 of the load-bearing structure 18 into a series of bladder compartments 24a-24h that each extend from the bottom of the boot 12 to a region 27 near the top of the boot 12. The compartments 24a-24h are separated along their lengths but are in fluid communication along the top region 27 of the fluid bladder 24 of panel 32. As shown in FIG. 1E, the panels 32a and 32b are separated by mechanical fastener 28 but remain in fluid communication through fluid flow channel 25, which allows fluid to pass between fluid compartments 24d and 24e. The depicted brace with the bladders formed by the depicted seams is only one embodiment of the systems described herein; in other embodiments the brace may include only one bladder or a plurality of separate bladders that may be separately inflatable or interconnected together. Additionally, the structure 18 may include perforations that allow circulation between bladders including, as discussed below, bladders within the internal compartment 78.

The inflation of the bladders 24 and 30 of structure 18 is achieved by inflation components 22 and 34 located in the upper portion of the boot 12. The inflation components 22 and 34 include cannulas that are adapted to convey fluid from an external source into the bladder regions 24 and 30, whereupon regions 24 and 30 inflate. More particularly, inflation component 22 is configured to inter-fit with the side panel 32a, such that when air or another fluid is inserted through component 22, the fluid flows into the upper region 27 then into compartments 24a-24h, thereby inflating such compartments to the desired level for supporting the injured leg. The inflation component 34 is configured to inter-fit with the bladder region 30 at top region 30a, and is adapted to inflate bladder regions 30a and 30b upon the application of the fluid. The lower-side portions 30c and 30d are separated from top region 30b by stitching, gluing or otherwise, so as to remain separated from the fluid received by region 30b (although in alternative configurations, regions 30c and 30d could be joined to region 30b and inflated).

In one aspect, the inflation of the bladders 24 and/or 30 converts structure 18 from flexible material to a rigid upper housing, suitable for use in treating a patient's fracture, edema or other indications. The inflation pressure can be adjusted as desired by the patient or by the physician. In certain implementations, the load-bearing structure 18 is inflated to a pressure of between about 3 psi to about 7 psi. Certain stable fractures and other indications may be treated by inflating structure 18 to an inflation pressure of about 5 psi. In another aspect, the separate inflation components 22 and 34 allow the foot region 30b and rear-leg region 24 to be separately inflated, which allows for customized sizing and is particularly helpful for patients who have excessive girth around either the lower leg or the foot. The components 22 and 34 may optionally include a one-way valve system that operates in cooperation with the pump mechanism 14 (as described below in reference to FIG. 4) to allow a patient to use its hand to adjust the fluid pressure in the load-bearing upper structure 18. In certain implementations, the structure 18 is inflated for use as a pneumatic apparatus. The brace may be combined with various systems, methods and apparatuses disclosed in U.S. Pat. Nos. 4,628,945, 6,322,530, and 6,775, 798, along with U.S. Publication 2003/0167057, the teachings of each of which are hereby incorporated by reference.

Although the boot 12 is inflated by pumping air into the internal bladders 24 and 30 of the load-bearing structure 18, other fluids may be used including heated water, cooled water, gel or any other fluid. To this end, the brace may be used in concert with a device for controlling the temperature of the fluid in the bladder. This can provide for therapeutic effect. Additionally, the brace may include an input valve and an output valve to allow for circulating fluid through the bladders. Exemplary valves, cooling systems, and other implementations are disclosed in U.S. Pat. Nos. 5,113,877, 5,230,335, 5,314,455, 5,277,695, 5,413,142, 5,441,533, and 5,466,250, the teachings of each of which is incorporated herein by reference. Additionally, in certain embodiments the bladder mechanism internal to the load-bearing structure 18 may be subdivided into separate bladder systems that are not in fluid communication, one of which may receive air, the other which may receive water, or some other material.

In operation, the patient applies the boot 12 to the limb by first deflating some or all of the fluid from the bladders 24 and/or 30 and disengaging the mechanical fastener 28 so that the boot 12 opens rearwardly, leaving a wide path for the patient to insert the foot and leg. The patient then inserts the foot through the opened rear region 31 of the boot 12 and slides the foot into the foot region (formed by the combination of regions 30b, 30c, and 30d). The mechanical fastener 28 is then re-engaged so that the back panel 32 and the front panel 30 envelop the user's lower leg. The load-bearing structure 18 is then inflated to the desired pressure using one or both of inflation mechanisms 22 and 34. Once the structure 18 is inflated, the patient may disconnect the hand pump 14 from the valves 22 and 34 and the patient is free to walk about with the boot 12 around its ankle. This adaptation allows the patient to select a boot having a foot region that is appropriately sized, even if the patient has excess girth around the lower leg.

Figure 1C:
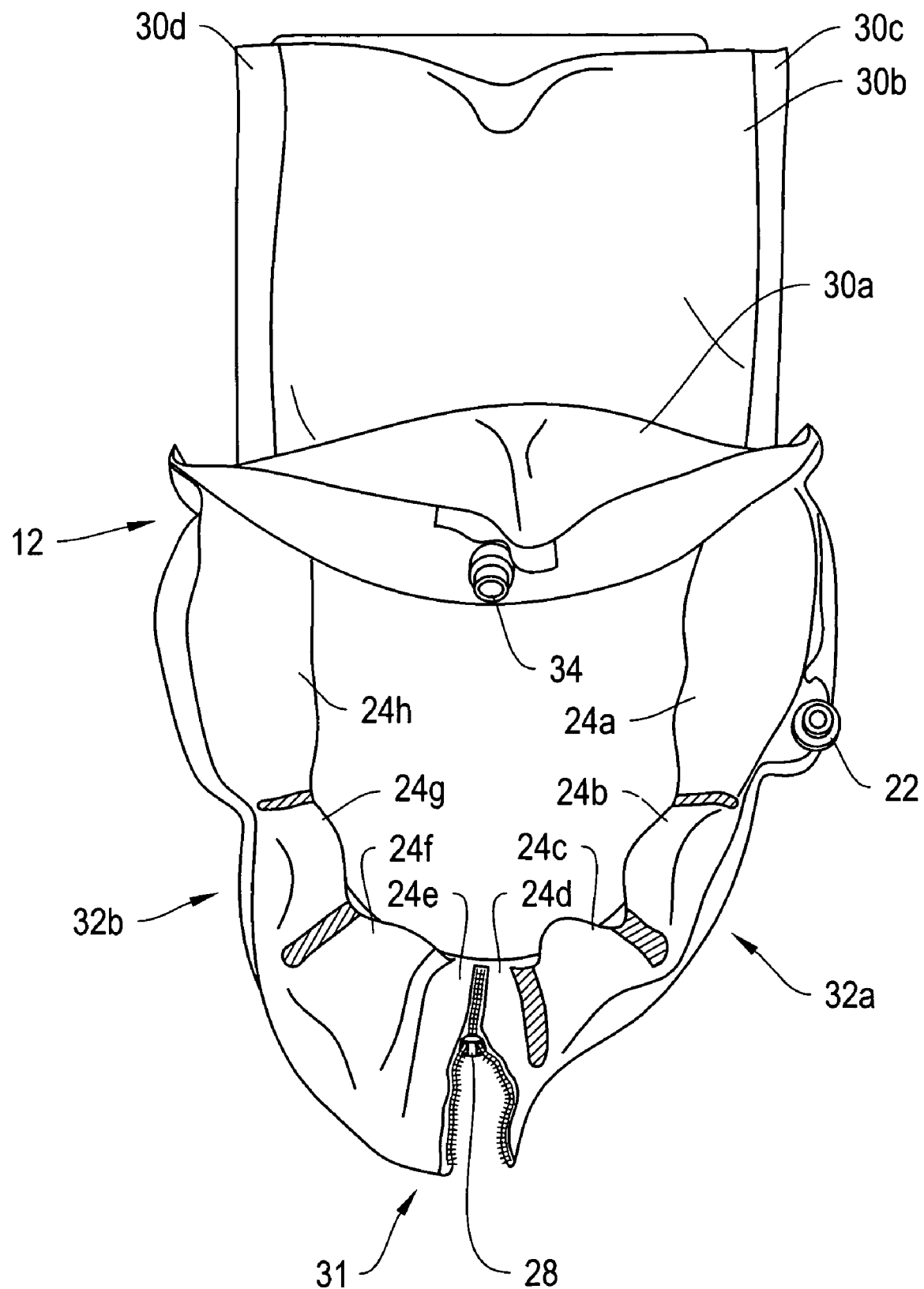

As shown in FIG. 1C and described above, the depicted boot 12 includes fastener 28. As shown, the fastener 28 is a rear zipper, but it will be understood that straps, hook and loop fasteners or any suitable sealing mechanism may be employed without departing from the scope of the invention. Further, although the boot 12 is depicted as a rear-loading brace, it may be constructed as a front-loading brace. In certain alternative embodiments, particularly where the patient does not have excessive girth around the lower leg, the boot 12 may be formed without using fastener 28, instead forming a unitary upper housing 18 with regions 30 and 32 configured as a continuous material through the use of a sealing mechanism on the side, at the front, or at a plurality of locations. This allows the brace to be configured as a sleeve that is pulled over the limb.

Figure 1D:
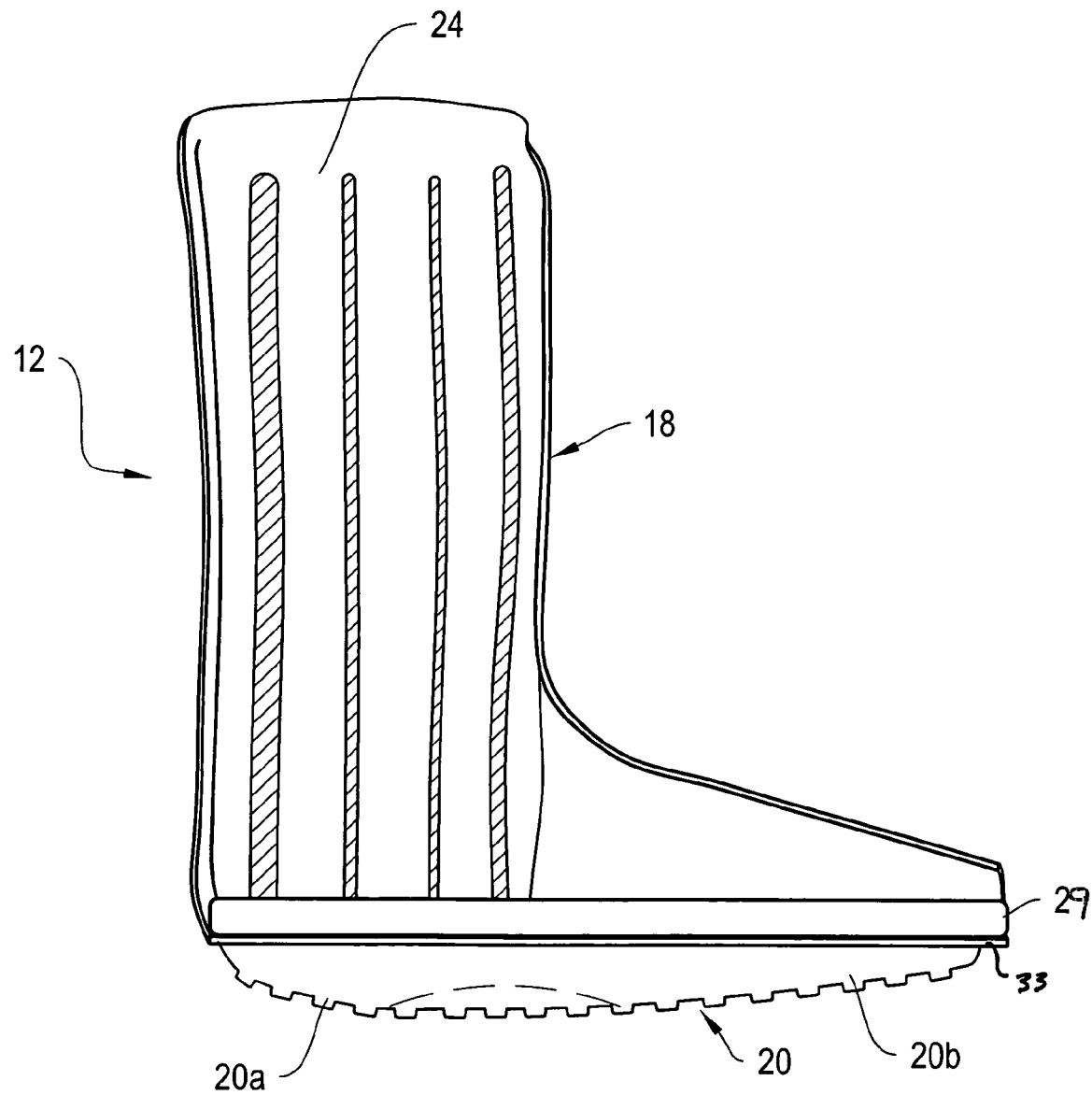
Figure 1E:
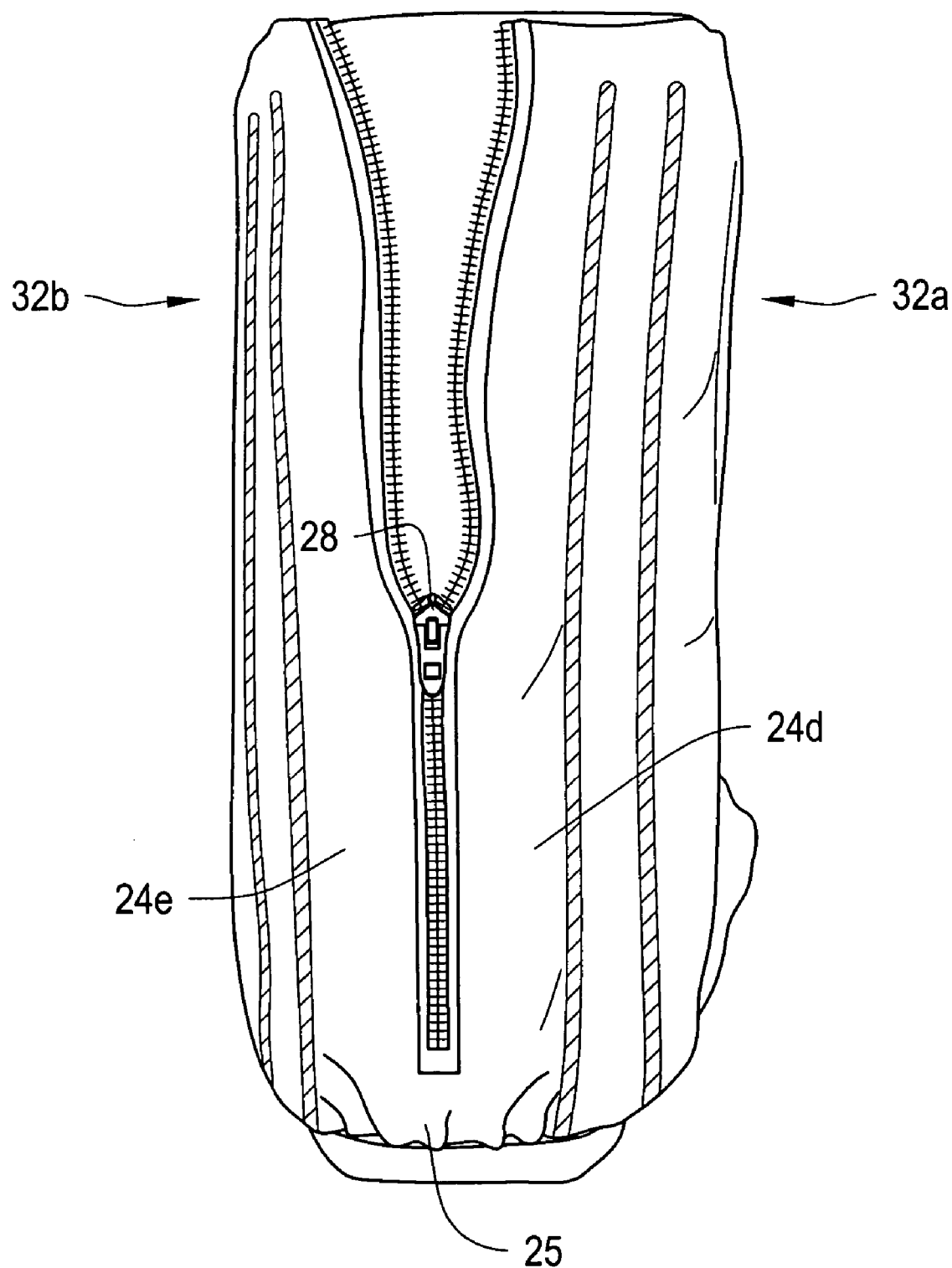

Also, as shown in cross-section in FIG. 1D, the depicted boot 12 includes sole 20 which comprises a rocker sole bottom formed of a relatively hard plastic material. As shown, the sole 20 is configured to have a thick region 20a near the patient's heel, and taper to a relatively thin region 20b near the patient's toes. The sole 20 may have a textured bottom for the purpose of providing the patient with a boot that can grip the surface of a road or floor as he or she walks. As shown in FIG. 1D, a pad 29 is included to support the patient's foot. A stiff support plate 33 is also included and fits on top of the region 20 and under the pad 29. An exemplary sole 20 that may be used with the boot 12 is found in U.S. patent application Ser. No. 10/769,587, filed Jan. 30, 2004, the entire contents of which are hereby incorporated by reference in their entirety.

Figure 2:
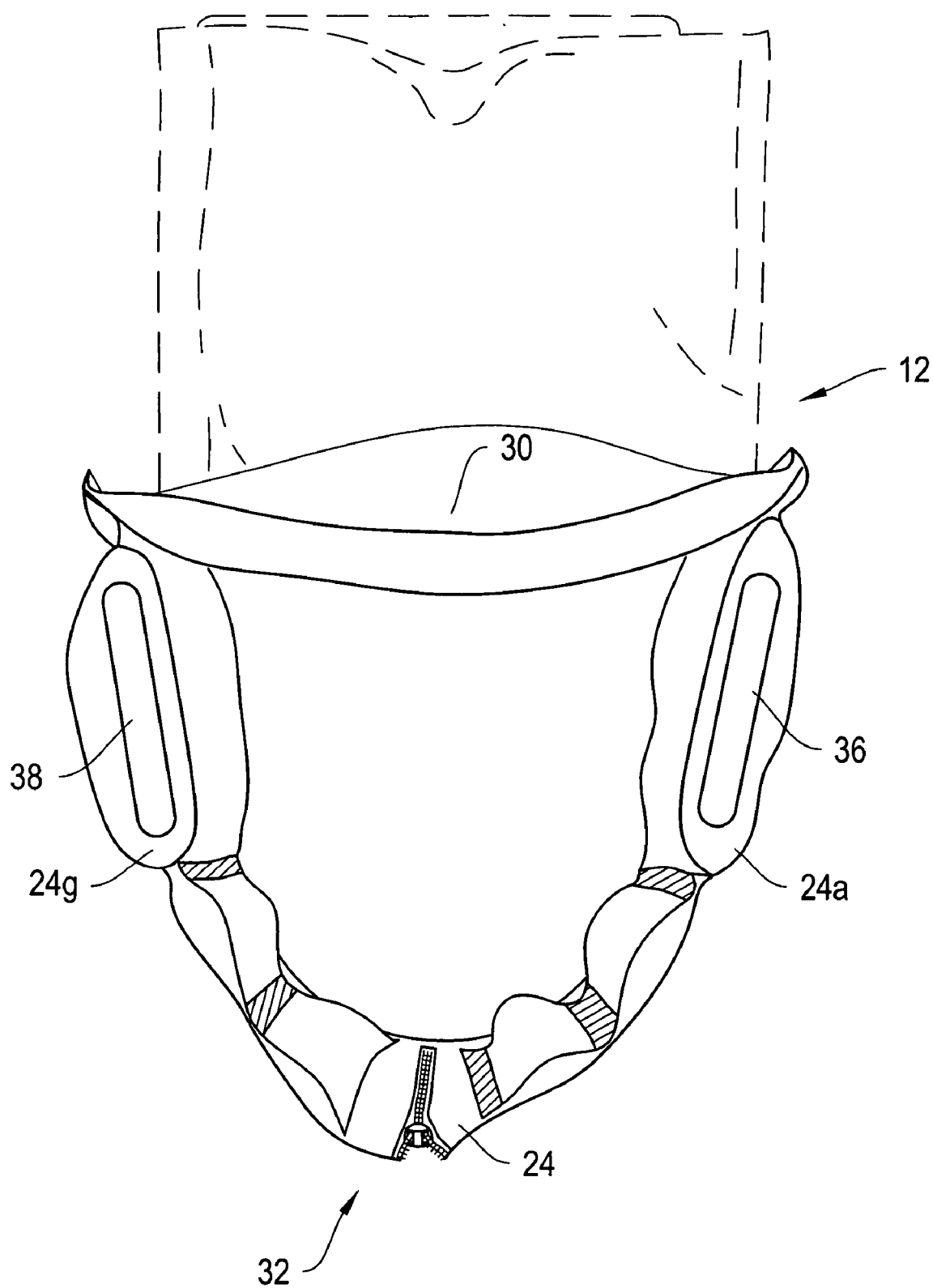
FIG. 2 depicts a top cross-sectional view of the brace of FIG. 1 having additional stiffening components.

In one aspect, the boot 12 functions as a brace for supporting a user's injured limb without requiring the use of a stiff shell or casing, such as those commonly used with prior art fracture braces. However, in certain optional configurations, one or more strengthening members, such as a plastic strip or thin metal elongated support member may be used with the boot 12. FIG. 2 depicts an example of such an optional embodiment. FIG. 2 depicts a top cross-sectional view of the boot 12, formed as shown above with respect to FIGS. 1A-1D, with the added feature of having strengthening support members 36 and 38 disposed within inflation compartments 24a and 24h, respectively. The support members 36 and 38 may be made from a plastic, sheet metal or other stiff supportive material. The support members 36 and 38 are fastened within the boot 12 by being stitched or glued or otherwise secured to the sole 20. The stiffening members 36 and 38 may be constructed from Teflon, polypropylene, thin sheet metal, or other rigid material, as appropriate. One or more of such strengthening members may be applied, as desired.

Figure 3A:
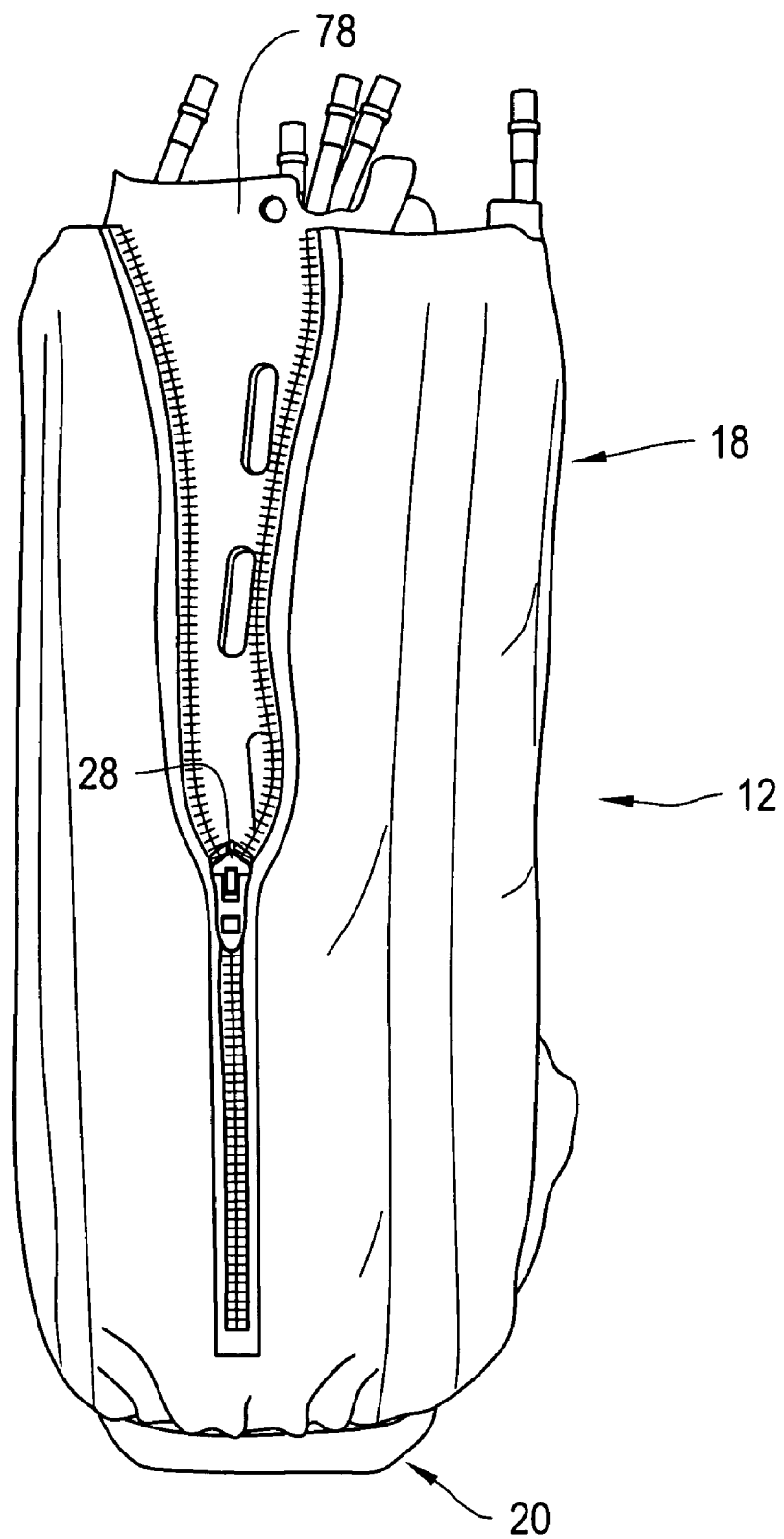
FIGS. 3A-3C depict an internal bladder system for use with a brace, as shown herein.
Figure 3B:
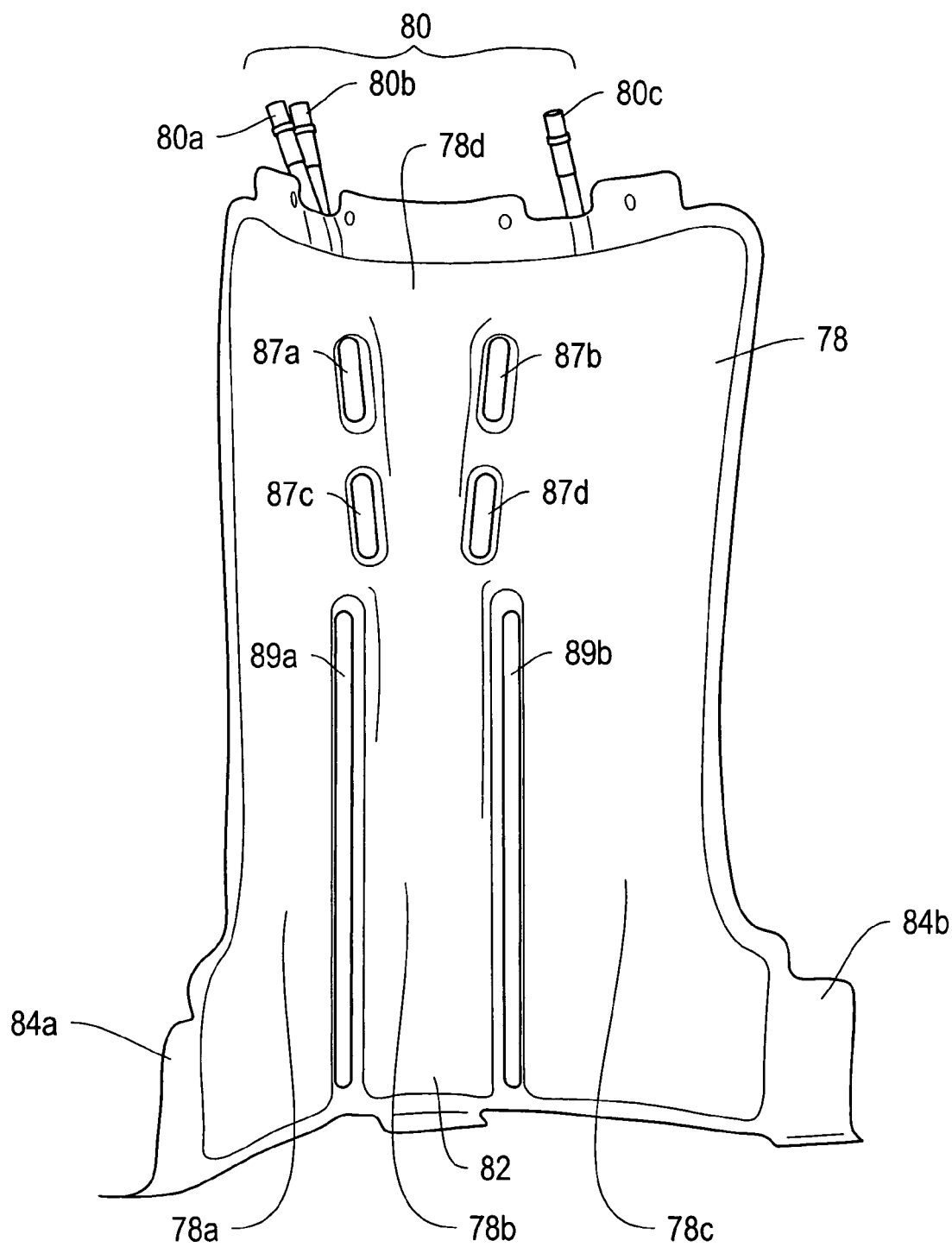
Figure 3C:
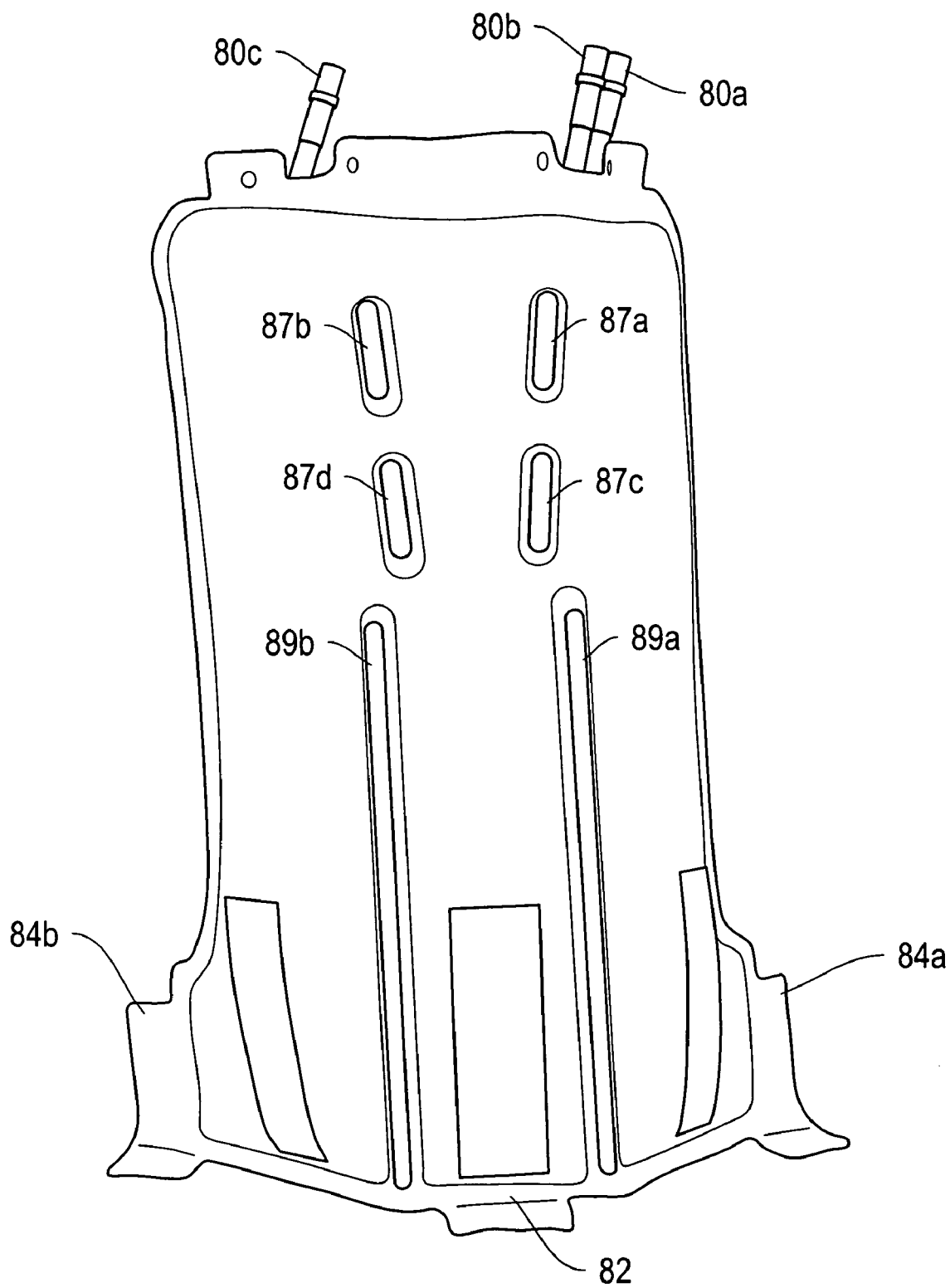

In certain implementations the boot 12 may also include a supplemental internal inflation system to further support the patient's injured limb. FIGS. 3A-3C depict an exemplary bladder system 78 that may be applied as an internal inflation system within the boot 12 described above. The bladder system 78 is made of a plurality of layers of fabric material that can be joined together to form a compliant, flexible soft wrap that fits around the patient's ankle. The material is sufficiently fluid-tight to support fluid that is delivered into the interior bladder system 78 and will inflate and provide compression around the patient's ankle.

As shown in FIG. 3A, the internal bladder system 78 is configured to fit within the load-bearing structure 18. FIGS. 3B and 3C show front and rear views of the bladder system 78 in an expanded format as if it were laid out across a flat table. The internal bladder system 78 has a rear-region 82 and two side-flaps 84a and 84b that are configured to wrap around the sides and rear of patient's lower leg and ankle region. In operation, the patient applies the fabric bladder system 78 to the foot before it is inflated by placing it around the ankle so that the lower midsection 82 is placed against the patient's heel. The two flaps 84a and 84b are then wrapped around the patient's foot so that they are disposed into the forward boot section. Once the system 78 is positioned around the lower region of the patient's leg, the leg is inserted into the boot 12 and the mechanical fastener 28 is closed so that patient's foot is secured within the internal bladder system 78 and within the boot 12. At that point, as described elsewhere herein, the patient can begin inflating the bladder system 78 and the boot 12.

In the depicted embodiment, the internal bladder system 78 is configured to be separately inflated from the load-bearing structure 18. To this end, the system 78 includes an inflation valve component 80 having one or more valves and cannula (e.g., 80a-80c) that the patient can use to insert fluid into the bladder system 78, thereby inflating the system 78 around the patient's ankle through the use of a pump, such as hand pump 14 shown in FIG. 4.

The system 78 also includes a series of inflation channels 78a-78c, with channels 78a and 78b being separated, in part, by a set of perforations within the structure 78 (perforations 87a, 87c, and 89a, which extend vertically along the panel 78), while channels 78b and 78c are separated, in part, by perforations 87b, 87d, and 89b (which also extend vertically along the panel 78). As shown, channels 78a, 78b, and 78c join in fluid communication in the region 78d, such that the insertion of air or other fluid through inflation port 80c will first cause fluid or air to flow into region 78d and then flow into the channels 78a-78c. The inflation ports 80a and 80b also allow the inflation of one or more of the regions within the inflation system 78.

In certain alternative configurations, each of the channels 78a, 78b, and 78c are configured to include a separate inflation mechanism. For example, inflation port 80a may be configured to inflate channel 78a, inflation port 80b configured to inflate channel 78b, and inflation port 80c configured to inflate channel 78c. In such configurations, each channel of 78a-78c is stitched or otherwise secluded from fluid correspondence with either of the other remaining two channels. Additional channels can be incorporated within the internal inflation mechanism 78, or fewer inflation bladders provided, such that one or more channels may be incorporated therein. Moreover, although the embodiment of FIGS. 3A-3C show an internal inflatable bladder 78 separate from the external bladders 24 and 30, in other embodiments, the brace may integrate the bladders to the main fluid cell of structure 18. Several ports could be made available to inflate the various compartments.

Figure 4:
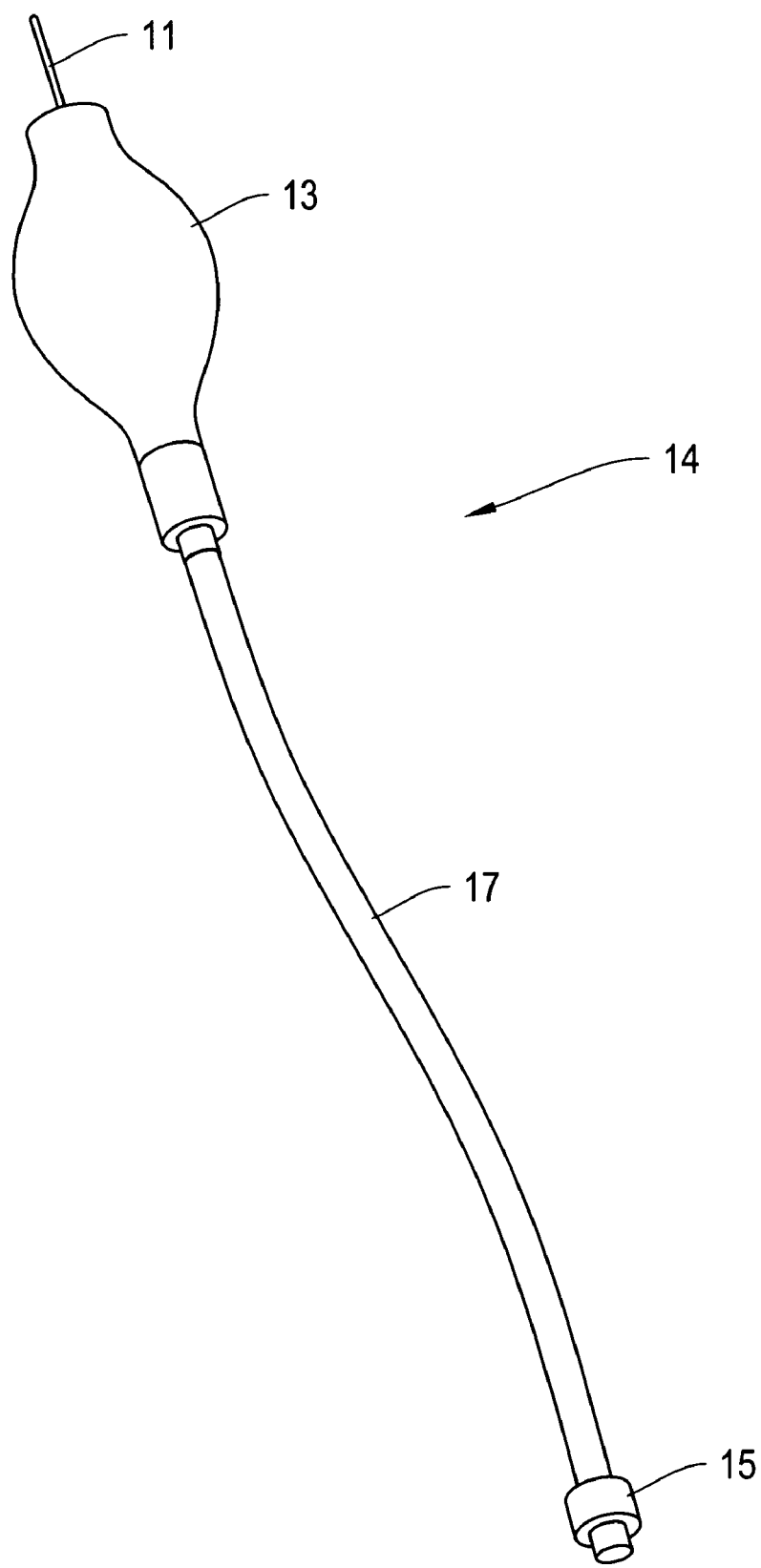
FIG. 4 depicts an exemplary pump for use with a brace, as shown herein.

FIG. 4 depicts a hand pump 14 that may be adapted for use with the boot 12 and/or internal inflation system 78 as described herein. More particularly, the inflation pump 14 includes a bulb 13 connected to a tube 17, and the tube 17 is connected to a nozzle 15 which may be applied to the inflation components 22 and 34 to allow the patient to inflate the inflation bladders 24, 30 and/or 78. The pump 14 also includes a pressure-relief valve 11, which can be used to release the pressure in the applicable bladder in a controlled manner. In certain configurations, an air compressor or other electro-mechanical device may be used to inflate the boot 12, such as a compressor that is located in a doctor's office or a hospital, which may be used to inflate the brace to the desired pressure before the patient leaves the office or the hospital.

Figure 5:
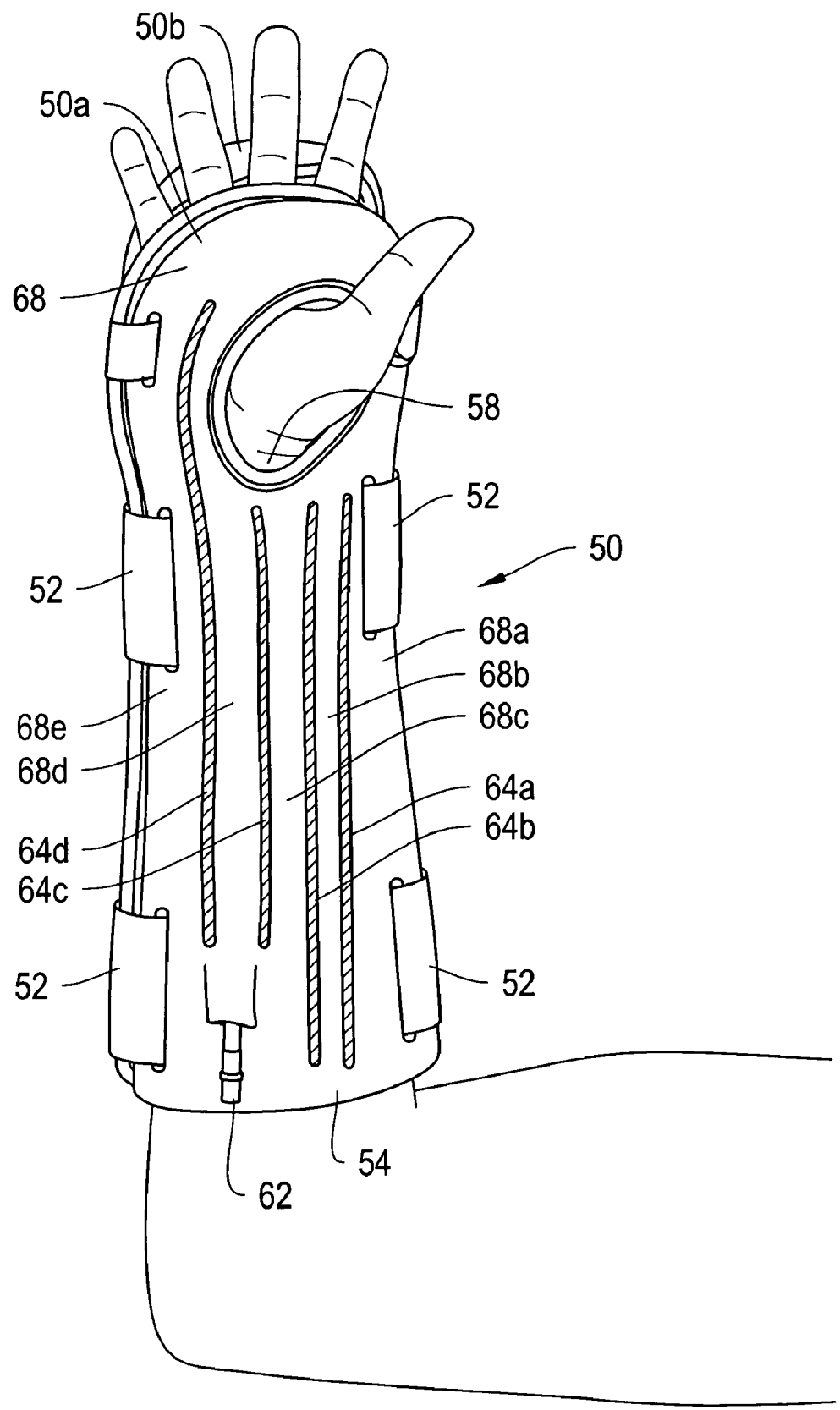
FIG. 5 depicts a first embodiment of a wrist brace according to another illustrative embodiment of the invention.

FIG. 5 depicts an alternate embodiment of the braces described herein. Specifically, FIG. 5 depicts a wrist brace 50 that includes an inflatable outer protective structure 54 formed from a lightweight flexible material, such as Nylon. The wrist brace 50 fits around the wrist and lower arm 48 of the patient. The wrist brace 50 comprises two sections, a lower section 50a and an upper section 50b, wherein the upper section 50a has a hole 58 for allowing the patient's thumb to fit there-through. The two sections 50a and 50b are joined by straps 52 so that the patient's arm 48 is secured within the brace 50. As depicted in FIG. 5, the inflatable outer protective structure 54 includes an inflation panel 68, comprising a series of inflation channels 68a-68e formed in the outer surface by the seams 64a-64d. A valve 62, similar to the inflation mechanisms 22 and 34 depicted in FIG. 1A-1E, is provided to allow the user to inflate the inflation panel 68. Optionally, an internal bladder system may be included to support the patient's limb, similar to the system 78 described above with reference to FIGS. 3A-3C. As discussed above the bladders may be combined into a single brace, or provided separately. In either case, the brace 50 depicted in FIG. 5, when inflated, provides a light-weight, rigid protective structure that can support a patient's injured limb while providing an internal fluid bladder than can offer a therapeutic effect to the injured limb or joint. Modifications to the wrist brace will be recognized by those of skill in the art and such modifications shall be deemed within the scope of the invention.

The systems and methods described herein provide a soft ankle brace that, among other things, is light-weight and provides prophylactic support to a patient while allowing the patient mobility. The brace is adjustable and configured to be fitted to patients having limbs of differing sizes, to allow the patient to obtain a more appropriately fitting brace. Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law. The teachings of all references cited herein are hereby incorporated by reference in their entireties.

The invention claimed is:

1. A brace for supporting an injured lower leg, comprising:
   a non-inflatable, rigid, lower housing for supporting the sole of a patient's foot,
   wherein the lower housing is a rocker sole, and
   an inflatable load-bearing upper housing having a plurality of longitudinally-extending compartments that are affixed to the lower housing and, when combined with the lower housing, the upper housing is adapted to substantially envelop a patient's lower leg,
   wherein the inflatable load-bearing upper housing, upon inflation, provides a rigid structural support by applying a sufficient pressure to the leg to support a leg fracture or other injury without using a stiff casing, and
   wherein the pressure applied to the leg is adjustable solely by inflation of the inflatable load-bearing upper housing.

2. The brace of claim 1, wherein the upper housing is a fluid bladder.

3. The brace of claim 1, wherein the upper housing is a fluid bladder that extends along a top surface of the user's foot.

4. The brace of claim 1, wherein the upper housing includes one or more fluid bladders that substantially circumferentiate the user's ankle and at least a portion of the user's shin and mid-calf.

5. The brace of claim 1, wherein the upper housing has a plurality of bladders for receiving fluid.

6. The brace of claim 1, wherein the upper housing provides primary support for the patient's leg.

7. The brace of claim 6, wherein the upper housing is adapted to be inflated to a pressure at least about 3 psi.

8. The brace of claim 1, wherein the upper housing extends down the patient's tibia, around the patient's heel and along the top of the patient's foot.

9. The brace of claim 1, wherein the upper housing envelops the patient's entire leg below the mid-calf region.

10. The brace of claim 1, further comprising a pump for inflating the upper housing.

11. The brace of claim 1, wherein the upper housing includes a first end, a second end, and a fastener adapted to connect the first and second ends behind the patient's leg.

12. The brace of claim 11, wherein the fastener is a zipper.

13. The brace of claim 1, wherein the upper housing is a sleeve adapted to be pulled onto a patient's foot.

14. The brace of claim 1, further comprising a support plate positionable between the lower housing and the patient's foot.

15. The brace of claim 1, wherein the lower housing includes a substantially flat top portion.

16. The brace of claim 1, wherein the lower housing includes a bottom portion that has a toe section, an arch section and a heel section.

17. The brace of claim 16, wherein the arch section is thicker than the heel section, and the heel section is thicker than the toe section.

18. The brace of claim 1, further comprising a flexible pad that is positionable between the lower housing and the sole of the patient's foot.

19. The brace of claim 1, wherein the inflatable load-bearing upper housing extends along the patient's foot and lower leg.

20. The brace of claim 1, wherein the inflatable load-bearing upper housing is inflated to a pressure between about 3 psi and about 7 psi.

21. The brace of claim 1, wherein the inflatable load-bearing upper housing is inflated to a pressure of about 5 psi.

22. The brace of claim 1, wherein the upper housing includes a first end, a second end, and a fastener adapted to bring the first and second ends into a fixed proximity.

23. The brace of claim 1, wherein the upper housing comprises a foot region and a rear-leg region that may be independently inflated.

24. A brace for supporting an injured lower leg, comprising:
   a non-inflatable, rigid, lower housing for supporting the sole of a patient's foot,
   wherein the lower housing is a rocker sole, and
   an inflatable load-bearing upper housing having a plurality of longitudinally-extending compartments that are affixed to the lower housing and, when combined with the lower housing, is adapted to substantially envelop a patient's lower leg,
   wherein the inflatable load-bearing upper housing, upon inflation, provides a rigid structural support by applying a sufficient pressure to the leg to support a leg fracture or other injury without using a stiff casing, and
   an internal bladder system that fits between the inflatable load-bearing upper housing and the patient's lower leg and is separately removable from the upper housing.

25. The brace of claim 24, wherein the internal bladder system has a plurality of inflation channels and at least one inflation mechanism.

26. The brace of claim 24, wherein the internal bladder system is independently adjustable with respect to the upper housing.

27. The brace of claim 24, wherein the upper housing provides primary support for the patient's leg.

28. A brace for supporting an injured lower leg, comprising:
- a non-inflatable, rigid, lower housing for supporting the sole of a patient's foot,
- wherein the lower housing includes a bottom portion that has a toe section, an arch section and a heel section,
- wherein the arch section is thicker than the heel section, and the heel section is thicker than the toe section, and
- an inflatable load-bearing upper housing having a plurality of longitudinally-extending compartments that are affixed to the lower housing and, when combined with the lower housing, the upper housing is adapted to substantially envelop a patient's lower leg,
- wherein the inflatable load-bearing upper housing, upon inflation, provides a rigid structural support by applying a sufficient pressure to the leg to support a leg fracture or other injury without using a stiff casing, and
- wherein the pressure applied to the leg is adjustable solely by inflation of the inflatable load-bearing upper housing.

29. A brace for supporting an injured lower leg, comprising:
- a non-inflatable, rigid, lower housing for supporting the sole of a patient's foot,
- wherein the lower housing includes a bottom portion that has a toe section, an arch section and a heel section,
- wherein the arch section is thicker than the heel section, and the heel section is thicker than the toe section, and
- an inflatable load-bearing upper housing having a plurality of longitudinally-extending compartments that are affixed to the lower housing and, when combined with the lower housing, is adapted to substantially envelop a patient's lower leg,
- wherein the inflatable load-bearing upper housing, upon inflation, provides a rigid structural support by applying a sufficient pressure to the leg to support a leg fracture or other injury without using a stiff casing, and
- an internal bladder system that fits between the inflatable load-bearing upper housing and the patient's lower leg and is separately removable from the upper housing.

* * * * *